United States Patent
Hayashi et al.

(10) Patent No.: US 8,104,330 B2
(45) Date of Patent: Jan. 31, 2012

(54) METHOD AND APPARATUS FOR ANALYSIS BY LIQUID CHROMATOGRAPHY

(75) Inventors: Morimasa Hayashi, Kyoto (JP); Yoshihiro Hayakawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 777 days.

(21) Appl. No.: 12/278,867

(22) PCT Filed: Feb. 9, 2006

(86) PCT No.: PCT/JP2006/302225
§ 371 (c)(1),
(2), (4) Date: Aug. 8, 2008

(87) PCT Pub. No.: WO2007/091323
PCT Pub. Date: Aug. 16, 2007

(65) Prior Publication Data
US 2010/0162801 A1    Jul. 1, 2010

(51) Int. Cl.
*G01N 30/30* (2006.01)
(52) U.S. Cl. ............. 73/61.57; 73/61.55; 210/198.2
(58) Field of Classification Search .......... 73/61.52, 73/61.55, 61.56, 61.57; 210/198.2; 436/161
See application file for complete search history.

(56) References Cited

U.S. PATENT DOCUMENTS

| | | | | |
|---|---|---|---|---|
| 4,233,156 A * | 11/1980 | Tsukada et al. | .............. | 210/101 |
| 6,955,760 B2 * | 10/2005 | Iwata | ...................... | 210/198.2 |
| 7,214,313 B2 * | 5/2007 | Hayashi et al. | ............ | 210/198.2 |
| 2003/0129761 A1 * | 7/2003 | Kakita et al. | .................. | 436/94 |
| 2005/0269264 A1 * | 12/2005 | Fermier et al. | ............ | 210/198.2 |

FOREIGN PATENT DOCUMENTS

| | | |
|---|---|---|
| JP | 11-281636 A | 10/1999 |
| JP | 2002-071660 A | 3/2002 |
| JP | 2003-098166 A | 4/2003 |
| WO | WO-99/61904 A1 | 12/1999 |

OTHER PUBLICATIONS

International Search Report for the Application No. PCT/JP2006/302225 mailed Mar. 20, 2006.
Hartmann, Eva et al., "Comparison of Reversed-Phase Liquid Chromatography and Hydrophilic Interaction/Cation-Exchange Chromatography for the Separation of Amphipathic α-Helical Peptides with L- and D-Amino Acid Substitutions in the Hydrophilic Face", Journal of Chromatography A, 2003, vol. 1009, pp. 61-71.
Hideko Kanazawa, "Temperature-Responsive Chromatography using Functional Polymers," Bunseki, 2004, vol. 6, pp. 303-308.

* cited by examiner

*Primary Examiner* — Daniel Larkin
(74) *Attorney, Agent, or Firm* — Cheng Law Group, PLLC

(57) ABSTRACT

In order to obtain a temperature gradient elution method which is rapid and accurate, a mobile phase (1) is supplied through two mobile-phase flow channels (2a) and (2b), mixed together, and introduced into the column (15) while the column (15) is made adiabatic. In this operation, the temperature of the mobile phase in one mobile-phase flow channel, i.e., the channel (2a), is regulated to a constant temperature higher than the upper limit of the target temperature range to be obtained in the column (15), while the temperature of the mobile phase in the other mobile-phase flow channel, i.e., the channel (2b), is regulated to a constant temperature lower than the lower limit of the target temperature range in the column (15). By controlling the flow rates in the two mobile-phase flow channels (2a) and (2b), the proportion in which these mobile-phase portions are mixed is changed with time to thereby change the temperature of the mobile phase in the column (15) with time. The temperature gradient elution method is thus conducted.

12 Claims, 9 Drawing Sheets

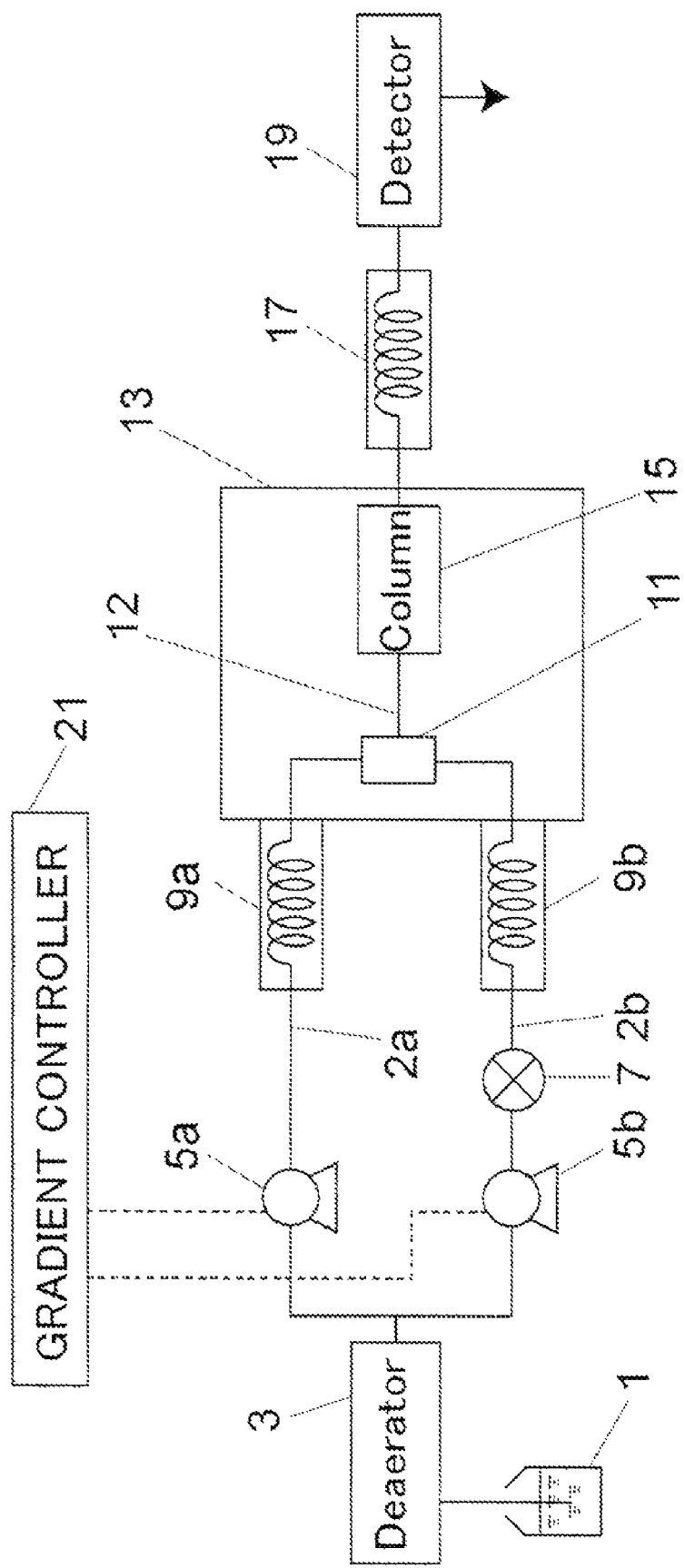

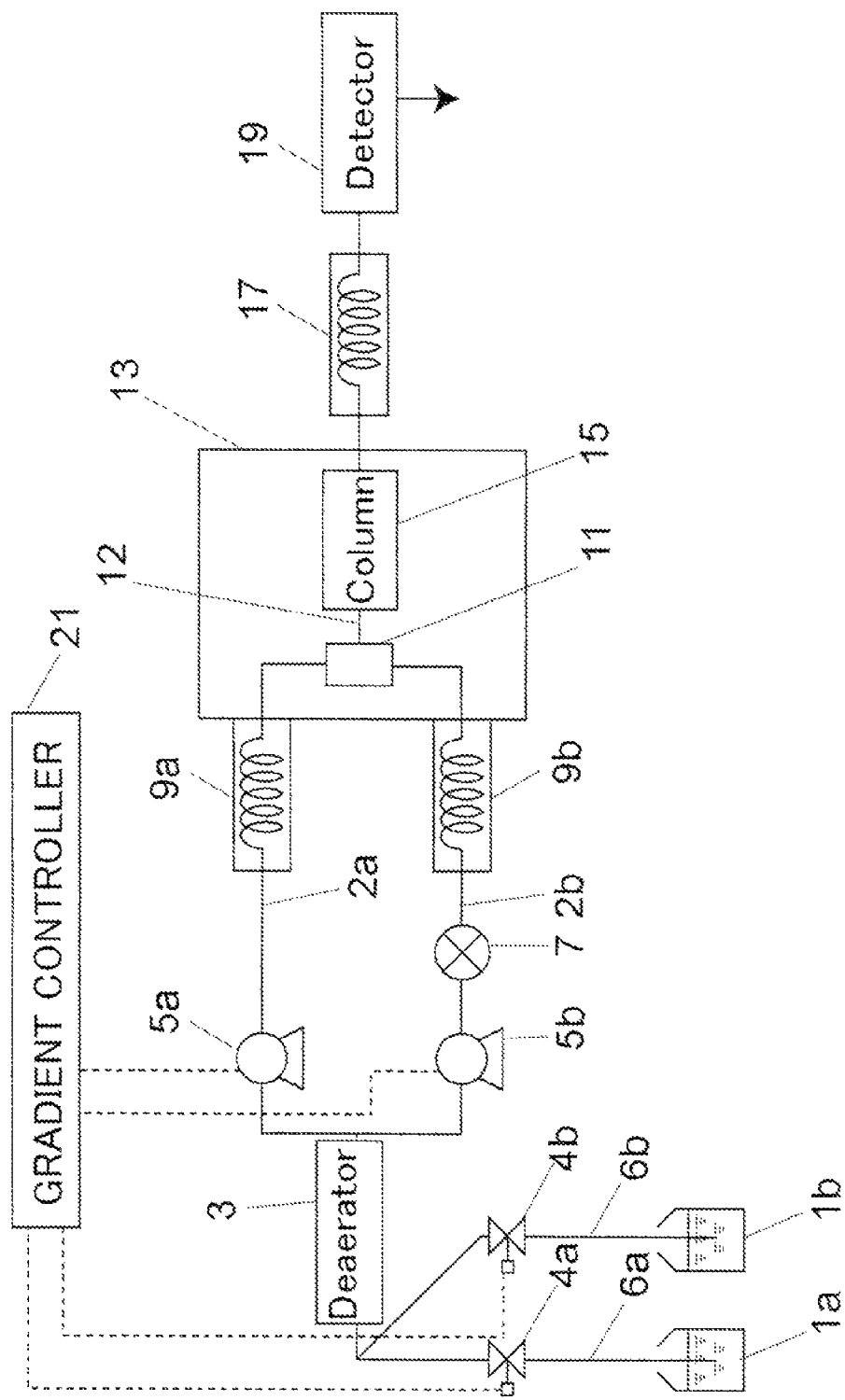

METHOD AND APPARATUS FOR ANALYSIS BY LIQUID CHROMATOGRAPHY

TECHNICAL FIELD

The present invention relates to liquid chromatography in which a sample to be analyzed is introduced into a separation column together with a mobile phase and then sample components separated by and eluted from the column are detected by a detector.

BACKGROUND ART

Liquid chromatography is widely used as a technique for analyzing sample components. More specifically, liquid chromatography is a separation technique utilizing a difference in the distribution of substances between two phases, i.e., between a stationary phase formed on the surface of a column packing material or on the inner surface of a capillary column and a mobile phase flowing through gaps in the packing material or the capillary column. Components of a sample pass through the column at different rates according to their respective chemical properties.

In a case where two or more substances having very different chemical properties from each other are analyzed all together, there is a case where it takes much time to analyze them. Therefore, in order to reduce analysis time while keeping a separation pattern, a mobile phase composition gradient elution method, in which the composition of a mobile phase is changed with time, is often used. The mobile phase composition gradient elution method is based on the fact that the distribution of substances is changed by changing the composition of a mobile phase.

FIG. 4 is a diagram showing a liquid chromatograph for mobile phase composition gradient elution.

As shown in FIG. 4, the liquid chromatograph includes mobile phase flow channels 2a and 2b for sending mobile phases 1a and 1b and liquid sending pumps 5a and 5b provided in the mobile phase flow channels 2a and 2b, respectively. The flow rate of each of the liquid sending pumps 5a and 5b is regulated by controlling the number of revolutions of motors. The mobile phase flow channels 2a and 2b join together at a mixer 11 where the mobile phases 1a and 1b are mixed and then flown into an analysis flow channel 12. The analysis flow channel 12 has a sample injection portion 7, a separation column 15 provided downstream of the sample injection portion 7 and a detector 19 provided downstream of the column 15.

A sample injected into the analysis flow channel 12 through the sample injection portion 7 is introduced into the separation column 15 by a mobile phase, obtained by mixing the mobile phases 1a and 1b by the mixer 11, to be separated into its components and then detected by the detector 19.

The flow rate of each of the liquid sending pumps 5a and 5b is controlled by a control unit 21 so as to be changed according to a predetermined mobile phase sending program to accomplish gradient elution.

In the case of using such a liquid chromatograph, as shown in FIG. 5, analysis is carried out by, for example, changing the sample retention power of the column 15 by gradually changing the composition of a mobile phase in such a manner that the concentration of a mobile phase A is decreased from 100% (initial) to 0% (final) and the concentration of a mobile phase B is increased from 0% (initial) to 100% (final). Particularly, such a gradient system, in which two or more liquid sending pumps are used to mix two or more mobile phases at a position downstream of the pumps, is called a "high-pres- It is to be noted that in FIG. 5, the coordinate A on the vertical axis represents the concentration of the mobile phase A being 100%, the coordinate B on the vertical axis represents the concentration of the mobile phase B being 100%, and the horizontal axis represents time.

Patent Document 1: Japanese Patent Application Laid-open No. 2003-98166

Non-Patent Document 1: Hideko Kanazawa, "Temperature-Responsive Chromatography", BUNSEKI, pp. 303-308, vol. 6, 2004

DISCLOSURE OF THE INVENTION

Problems to be Solved by the Invention

However, in the case of using the mobile phase composition gradient elution method, there is a case where a detector responds to a change in the composition of a mobile phase so that a base line fluctuates. For this reason, there is a case where the mobile phase composition gradient elution method cannot be used for analysis depending on the requirements for a mobile phase or the kind of detection method used.

Further, there is also a case where the purpose of analysis cannot be sufficiently accomplished by simply using the mobile phase composition gradient elution method.

On the other hand, as an alternative to the mobile phase composition gradient elution method, a temperature gradient elution method has been proposed in which the temperature of a column and its vicinity is changed with time (see, for example, Non-Patent Document 1). The temperature gradient elution method is based on the fact that the distribution of substances is changed also by temperature change. According to the temperature gradient elution method, the temperature of a column is externally changed to change the temperature of a mobile phase in the column.

However, such a method proposed as an alternative to the mobile phase composition gradient elution method is difficult to rapidly and accurately change the temperature of a column because thermal conductivity varies depending on the thermal capacity of a heat medium, the thermal conductivities of the heat medium and a column tube material, and the temperature difference between the heat medium and a column tube. Further, there is also a problem that a temperature gradient is produced in the cross-sectional direction of the column so that peak shape deterioration is likely to occur. For these reasons, the temperature gradient elution method has not been popular.

It is therefore an object of the present invention to provide a rapid and accurate temperature gradient elution method.

Means for Solving the Problems

Attention has been focused on the fact that the temperature of a mobile phase can be rapidly regulated by mixing two streams of the mobile phase having different temperatures at any mixing ratio. Based on the fact, the present invention is intended to achieve the above object by adjusting the temperatures of two streams of a mobile phase flowing through two flow channels to different constant temperatures, mixing them at any mixing ratio, and introducing the mixed mobile phase into a thermally-insulated column.

More specifically, the present invention is directed to a temperature gradient elution method for analysis by liquid chromatography in which a sample to be analyzed is introduced into a separation column together with a mobile phase and then sample components separated by and eluted from the column are detected by a detector, the method including:

keeping the column adiabatic;

mixing two streams of the mobile phase supplied through two mobile phase flow channels and introducing the mixed mobile phase into the column, wherein the temperature of the mobile phase supplied through one of the mobile phase flow channels is set to a constant temperature higher than the upper limit of a target temperature range of the mobile phase in the column and the temperature of the mobile phase supplied through the other mobile phase flow channel is set to a constant temperature lower than the lower limit of the target temperature range of the mobile phase in the column; and changing the temperature of the mobile phase in the column with time by changing the mixing ratio between the two streams of the mobile phase with time by regulating the flow rates of the two streams of the mobile phase flowing through the two mobile phase flow channels.

By changing the mixing ratio between the two streams of the mobile phase with time, it is possible to change the temperature of the mobile phase in the column from one constant temperature to another, step-wise, or it is possible to continuously change the temperature of the mobile phase in the column from low to high temperatures or from high to low temperatures. According to the present invention, both the step-wise change and the continuous change can be achieved. The step-wise change has the advantage that control is simple. On the other hand, in a case where the mixing ratio is continuously changed with time, it is possible to create a temperature gradient along the moving direction of the mobile phase in the column.

According to the present invention, the temperature of an eluate from the column is also changed with time. Therefore, there is a case where detector sensitivity varies or a base line fluctuates with temperature depending on the kind of detector used. In order to avoid such a problem, it is preferred that the temperature of an eluate from the column is adjusted to a constant temperature before the eluate is introduced into the detector.

When the flow rate of the mobile phase introduced into the column is changed, the retention time of the peak is also changed. Therefore, in order to carry out analysis more accurately, it is preferred that the flow rate of the mobile phase introduced into the column is kept constant by regulating the flow rates of two streams of the mobile phase flowing through the two mobile phase flow channels.

In the case of liquid chromatography analysis which can be carried out by a mobile phase composition gradient elution method, the analysis may be carried out using the temperature gradient elution method according to the present invention in combination with a mobile phase composition gradient elution method, in which the composition of the mobile phase supplied through the two mobile phase flow channels is changed with time, to enhance the effect of gradient elution.

Further, the present invention is also directed to a liquid chromatograph including: a separation column; a thermal insulating container for receiving the column; a first mobile phase flow channel having a liquid sending pump and a constant-temperature unit whose temperature is set to a constant temperature higher than the upper limit of a target temperature range of a mobile phase in the column; a second mobile phase flow channel which has a liquid sending pump different from the liquid sending pump provided in the first mobile phase flow channel and a constant-temperature unit whose temperature is set to a constant temperature lower than the lower limit of the target temperature range of the mobile phase in the column and which sends the same mobile phase as sent through the first mobile phase flow channel; a mixer for mixing the mobile phase supplied through the first mobile phase flow channel and the mobile phase supplied through the second mobile phase flow channel and sending the mixed mobile phase to the column; a sample injector for injecting a sample to be analyzed into a flow channel for supplying the mobile phase to the column; a detector provided downstream of the column to detect sample components separated by and eluted from the column; and a gradient controller for regulating the flow rates of the liquid sending pumps provided in the first and second mobile phase flow channels to change the mixing ratio with time between the mobile phases in the mixer. By using such a liquid chromatograph, it is possible to change the temperature of the mobile phase in the column with time, thereby enabling temperature gradient elution to be carried out.

A temporal change in the mixing ratio between two streams of the mobile phase controlled by the gradient controller includes a step-wise change and a continuous change. In order to create a temperature gradient along the moving direction of the mobile phase in the column, the gradient controller regulates the flow rates of the liquid sending pumps provided in the first and second mobile phase flow channels in such a manner that the mixing ratio is continuously changed with time.

The liquid chromatograph according to the present invention preferably further includes a constant-temperature unit provided between the column and the detector to adjust the temperature of an eluate from the column to a constant temperature.

A preferred embodiment of the gradient controller is one which can regulate the flow rates of the liquid sending pumps provided in the first and second mobile phase flow channels so that the flow rate of the mobile phase introduced into the column becomes constant.

The liquid chromatograph according to the present invention may further include a mobile phase composition gradient system provided in the first and second mobile phase flow channels to change the composition of the mobile phase with time.

The position of the sample injector is not particularly limited as long as the sample injector can inject a sample into a flow channel for supplying the mobile phase to the column. For example, the sample injector can be provided in the first or second mobile phase flow channel or in a flow channel provided between the mixer and the column.

The adjustable temperature range of the mobile phase for gradient analysis depends on the composition of the mobile phase, but the upper limit of the temperature range of the mobile phase can be set to a quite high temperature because each of the constant-temperature units provided in the mobile phase flow channels is subjected to a high pressure resulting from the flow resistance of the column, and therefore, the boiling point of the mobile phase is increased.

Effect of the Invention

As described above, the method and apparatus for analysis by liquid chromatography according to the present invention make it possible to easily change the temperature of a mobile phase in the column because the temperatures of two streams of the mobile phase flowing through the two flow channels are adjusted to different constant temperatures, and then the two streams of the mobile phase are mixed at any mixing ratio to introduce the mixed mobile phase into the column designed to prevent heat from escaping therefrom. Therefore, it is possible to achieve a rapid temperature gradient elution method previously difficult to achieve.

Further, unlike a conventional temperature gradient elution method in which a column is externally heated or cooled by a heat medium, the method and apparatus according to the present invention make it possible to prevent a temperature gradient from being produced in the cross-sectional direction of the column, thereby preventing peak shape deterioration.

Therefore, according to the present invention, it is possible to achieve a rapid and accurate temperature gradient elution method.

According to the present invention, by continuously changing the mixing ratio with time, it is possible to create a temperature gradient in the flow direction of the mobile phase in the column, thereby suppressing the diffusion of substances in the column due to a concentration effect resulting from the temperature gradient and therefore making it possible to achieve efficient separation.

By adjusting the temperature of an eluate from the column to a constant temperature before the eluate is introduced into the detector, it becomes possible to use a detector sensitive to temperature change, such as a differential refractometer detector.

By keeping the flow rate of the mobile phase introduced into the column constant, it is possible to improve the reproducibility of the retention time of the peak, thereby improving measurement accuracy.

By using the temperature gradient elution method according to the present invention in combination with a mobile phase composition gradient elution method, it is possible to achieve more efficient gradient elution.

BRIEF DESCRIPTION OF THE DRAWINGS

FIG. 1C is a diagram showing the flow channel configuration of a high-performance liquid chromatograph according to still another embodiment of the present invention;

FIG. 3C is a diagram showing the flow channel configuration of a high-performance liquid chromatograph according to still another embodiment of the present invention;

Figure 1A:
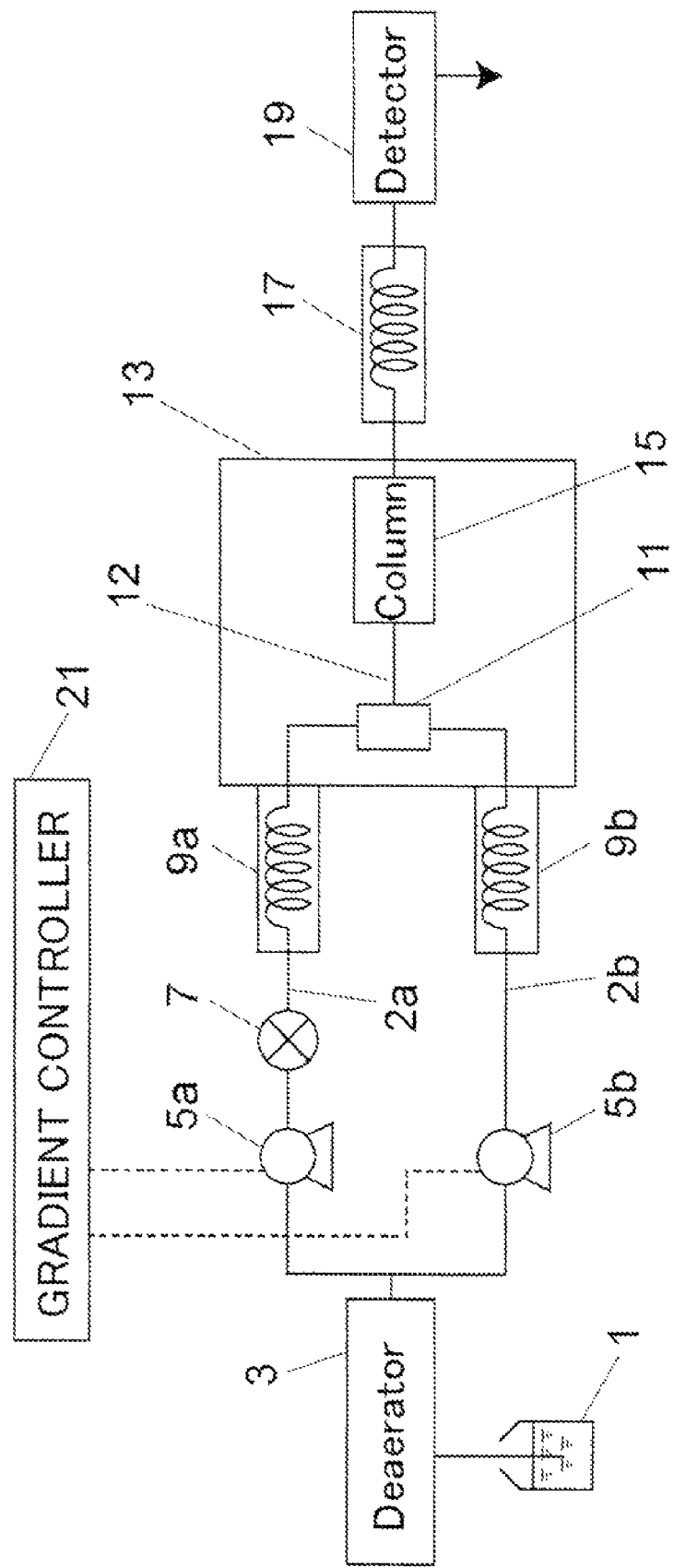
FIG. 1A is a diagram showing the flow channel configuration of a high-performance liquid chromatograph according to one embodiment of the present invention.

DESCRIPTION OF THE REFERENCE NUMERALS 1, 1a, 1b mobile phase
2a, 2b mobile phase flow channel
3 deaerator
5a, 5b liquid sending pump
7 sample injector
9a, 9b, 17 constant-temperature unit
11 mixer
12 analysis flow channel
13 thermal insulating container
15 column
19 detector
21 gradient controller

BEST MODE FOR CARRYING OUT THE INVENTION

Hereinbelow, the present invention will be described in detail with reference to the following embodiments.

FIG. 1A is a diagram showing the flow channel configuration of a high-performance liquid chromatograph according to one embodiment of the present invention. The high-performance liquid chromatograph includes two mobile phase flow channels $2a$ and $2b$ that branch off from a mobile phase flow channel for sending a mobile phase 1 passed through a deaerator 3 for removing a gas from the mobile phase 1. One of the mobile phase flow channels, that is, the mobile phase flow channel $2a$, has a liquid sending pump $5a$, a sample injector 7 and a constant-temperature unit $9a$ whose temperature is set to a constant temperature lower than the lower limit of a target temperature range of the mobile phase in a column. The other mobile phase flow channel $2b$ has a liquid sending pump $5b$ and a constant-temperature unit $9b$ whose temperature is set to a constant temperature higher than the upper limit of the target temperature range of the mobile phase in the column.

The two mobile phase flow channels $2a$ and $2b$ are connected to a mixer 11. A separation column 15 for separating a sample into its components is connected to a flow channel 12 provided downstream of the mixer 11, and a constant-temperature unit 17 is connected downstream of the column 15, and a detector 19 for detecting sample components separated by and eluted from the column 15 is connected downstream of the constant-temperature unit 17. The constant-temperature unit 17 can be omitted depending on the kind of the detector 19.

The mixer 11 and the column 15 are received in a thermal insulating container 13 to prevent heat from escaping from them. As shown in FIG. 1, a region from the exits of the constant-temperature units $9a$ and $9b$ to the exit of the column 15 is preferably received in the thermal insulating container 13.

The liquid sending pumps $5a$ and $5b$ are connected to a gradient controller 21. The gradient controller 21 regulates the flow rates of the liquid sending pumps $5a$ and $5b$ provided in the mobile phase flow channels $2a$ and $2b$, respectively, to regulate the flow rates of two streams of the mobile phase flowing through the mobile phase flow channels $2a$ and $2b$ so that the mixing ratio between the two streams of the mobile phase mixed by the mixer 11 is changed with time.

Each of the constant-temperature units $9a$, $9b$, and 17 has a tube made of a high thermal conductive material such as stainless steel, and the tube is heated or cooled by an aluminum block or air as a medium. The mixer 11, the column 15 and their pipes are made of a low thermal conductive material such as polyether ether ketone (PEEK).

As can be seen from the flow channel configuration shown in FIG. 1A, the mobile phase 1 is passed through the deaerator 3 to remove air bubbles therefrom, and is then flown into two flow channels $2a$ and $2b$. The flow rate of the mobile phase 1 flowing through the flow channel $2a$ and the flow rate of the mobile phase 1 flowing through the flow channel 2b are regulated by the liquid sending pumps 5a and 5b controlled by the gradient controller 21, respectively, so that the ratio between these flow rates is set to any value. The temperature of the mobile phase 1 flowing through the flow channel 2a and the temperature of the mobile phase 1 flowing through the flow channel 2b are adjusted to different temperatures by the constant-temperature units 9a and 9b, respectively, and then the mobile phase 1 flowing through the flow channel 2a and the mobile phase 1 flowing through the flow channel 2b are mixed by the mixer 11, and then introduced into the column 15. In general, the flow rates of the liquid sending pumps 5a and 5b are controlled so that the flow rate of the mixed mobile phase becomes constant, and the temperature of the constant-temperature unit 9a is set to be lower than the lower limit of a target temperature range, and the temperature of the constant-temperature unit 9b is set to be higher than the upper limit of the target temperature range. For example, in a case where temperature gradient elution is carried out by a linear temperature gradient from 30 to 70° C. under conditions where the flow rate of the mobile phase in the column 15 is 1.0 mL/min, the temperatures of the constant-temperature units 9a and 9b are set to 25° C. and 75° C., respectively, and the flow rate of the liquid sending pump 5a is changed from 0.9 to 0.1 mL/min in one minute, and at the same time the flow rate of the liquid sending pump 5b is changed from 0.1 to 0.9 mL/min in one minute. Such changes in the flow rates of the liquid sending pumps 5a and 5b are controlled by the gradient controller 21. In this case, when the liquid chromatograph is operated in ideal conditions, the temperature of the mobile phase is continuously and lineally changed from 30 to 70° C. in one minute with time.

An eluate from the column 15 is introduced into the constant-temperature unit 17 to adjust the temperature of the eluate to a constant temperature, and is then introduced into the detector 19 to detect sample components separated by the column 15.

Hereinbelow, the high-performance liquid chromatograph according to the present invention will be described in more detail.

For the column 15, for example, a reverse phase chromatography column Shim-PackFC-ODS® (inner diameter: 3 mm, length: 100 mm) is used. It is to be noted that the column 15 is not particularly limited as long as its column tube is made of a low thermal conductive material such as PEEK.

For the detector 19, an absorbance detector, a fluorescence detector, a differential refractometer detector, an evaporative light scattering detector, or the like can be used. If necessary, a mass spectrometer can be further connected to the detector 19.

For the mobile phase, for example, a mixture of water and acetonitrile is used. It is to be noted that the mobile phase is selected depending on a sample to be analyzed, and there are no restrictions on the kind, temperature, and pH of the mobile phase.

Figure 1B:
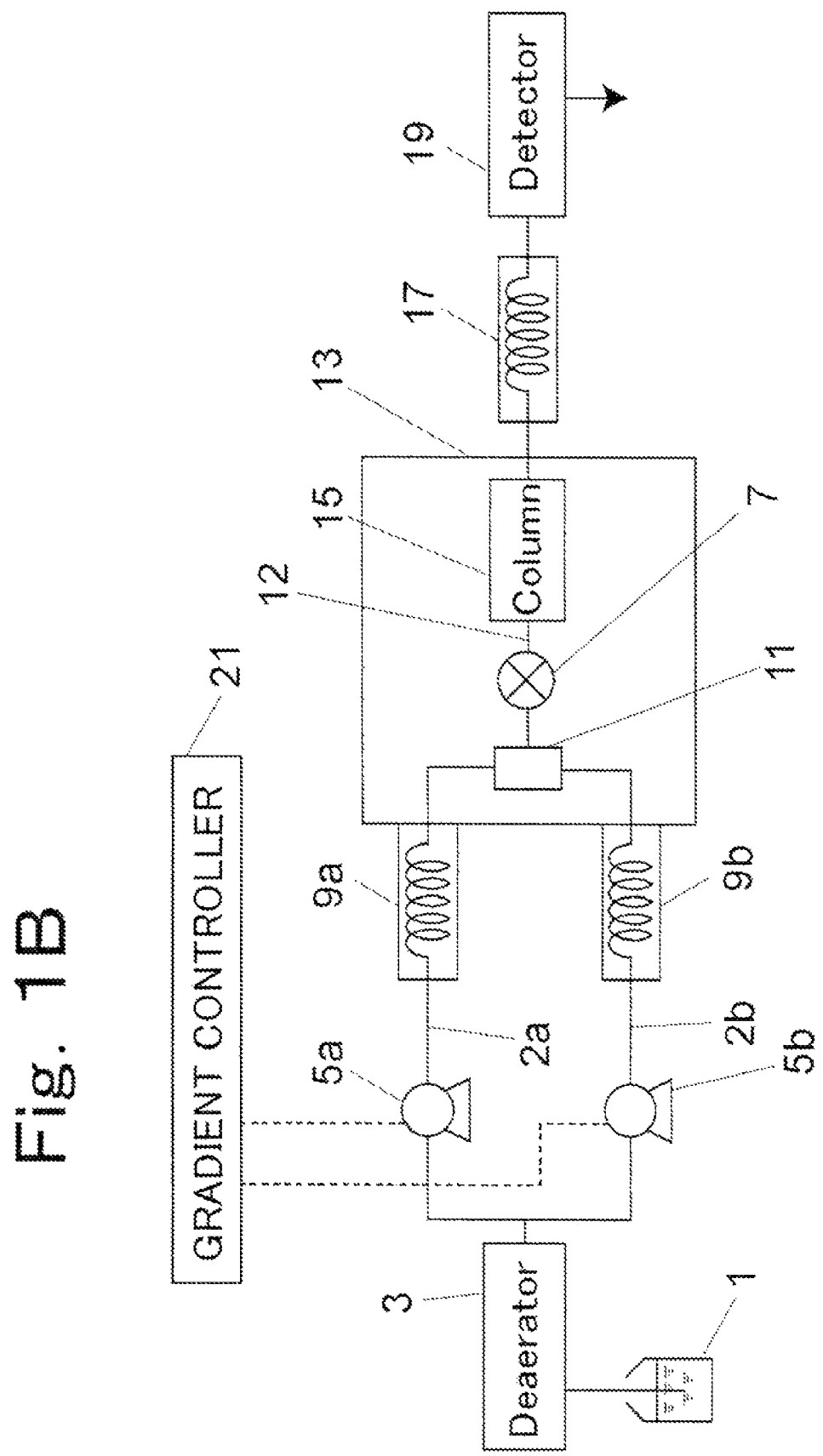
FIG. 1B is a diagram showing the flow channel configuration of a high-performance liquid chromatograph according to another embodiment of the present invention.

FIG. 1B is a diagram showing the flow channel configuration of a high-performance liquid chromatograph according to another embodiment of the present invention. The high-performance liquid chromatograph shown in FIG. 1B is different from the high-performance liquid chromatograph shown in FIG. 1A in the position of the sample injector 7. In the high-performance liquid chromatograph shown in FIG. 1B, the sample injector 7 is provided in the flow channel 12 between the mixer 11 and the column 15.

The sample injector 7 may be provided between the constant-temperature unit 9a or 9b and the mixer 11.

Figure 2:
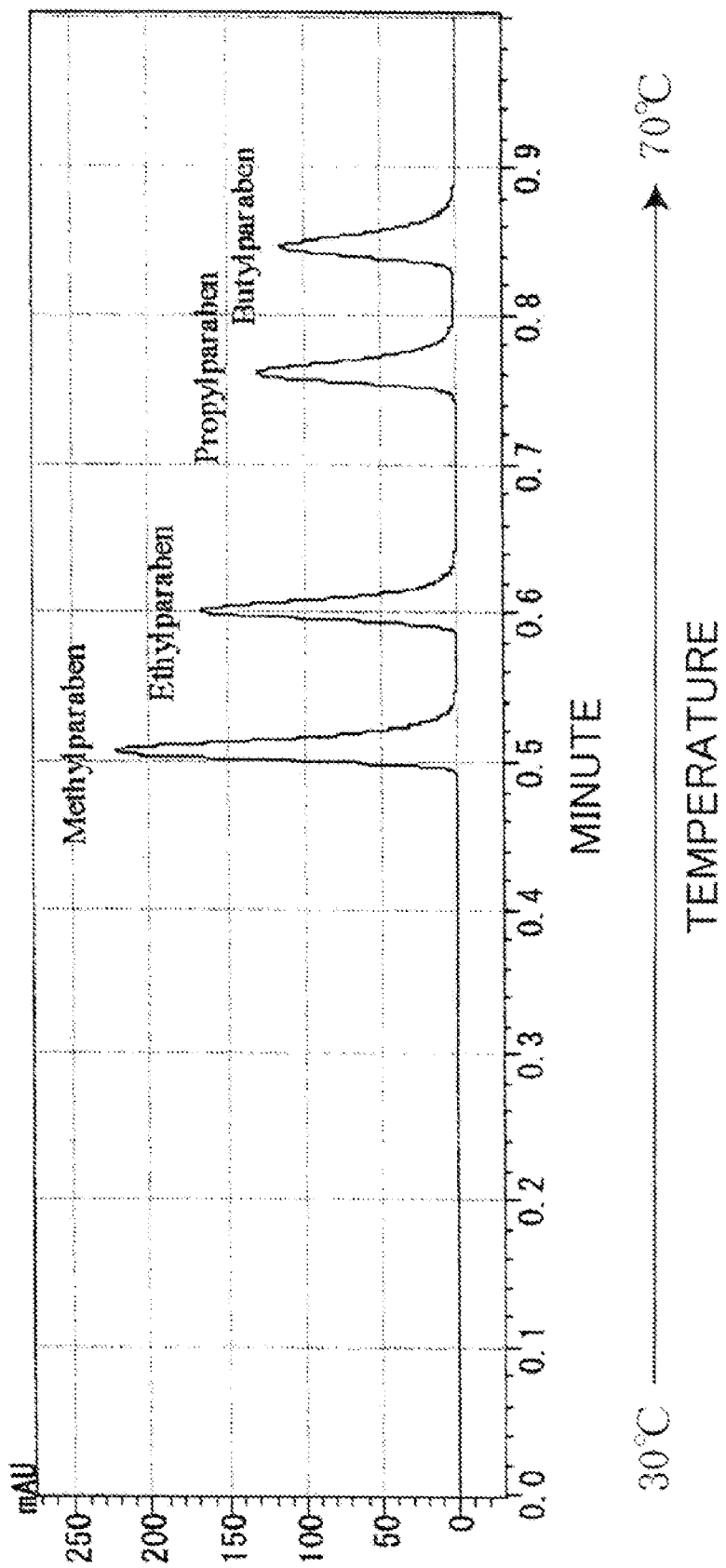
FIG. 2 is a chromatogram obtained by carrying out temperature gradient elution using the high-performance liquid chromatograph shown in FIG. 1A.

Measurement conditions are as follows.
(1) Analytical conditions
Column: Shim-PackFC-ODS® (inner diameter 3 mm, length: 100 mm)
Mobile phase: mixture of water and acetonitrile (1:1 in volume ratio)
Flow rate: 1.0 mL/min
Temperature: temperature gradient from 30 to 70° C. in one minute
(2) Detection conditions
Detector: absorbance detector
Detection wavelength: 260 nm FIG. 2 is a chromatogram obtained by analyzing a standard mixture of alkyl parabens, including methyl paraben, ethyl paraben, propyl paraben and butyl paraben, with the use of the high-performance liquid chromatograph shown in FIG. 1A under the above-described measurement conditions. In FIG. 2, the horizontal axis represents time, and the vertical axis represents absorbance (mAU) indicating detected intensity. The temperature of the mobile phase is linearly increased with time from 30 to 70° C.

As can be seen from FIG. 2, methyl paraben, ethyl paraben, propyl paraben and butyl paraben were eluted from the column within one minute and well separated from one another. This result indicates that the temperature gradient elution method according to the present invention enables rapid separation.

Hereinbelow, high-performance liquid chromatographs according to other embodiments of the present invention will be described with reference to FIGS. 3A and 3B.

Figure 3A:
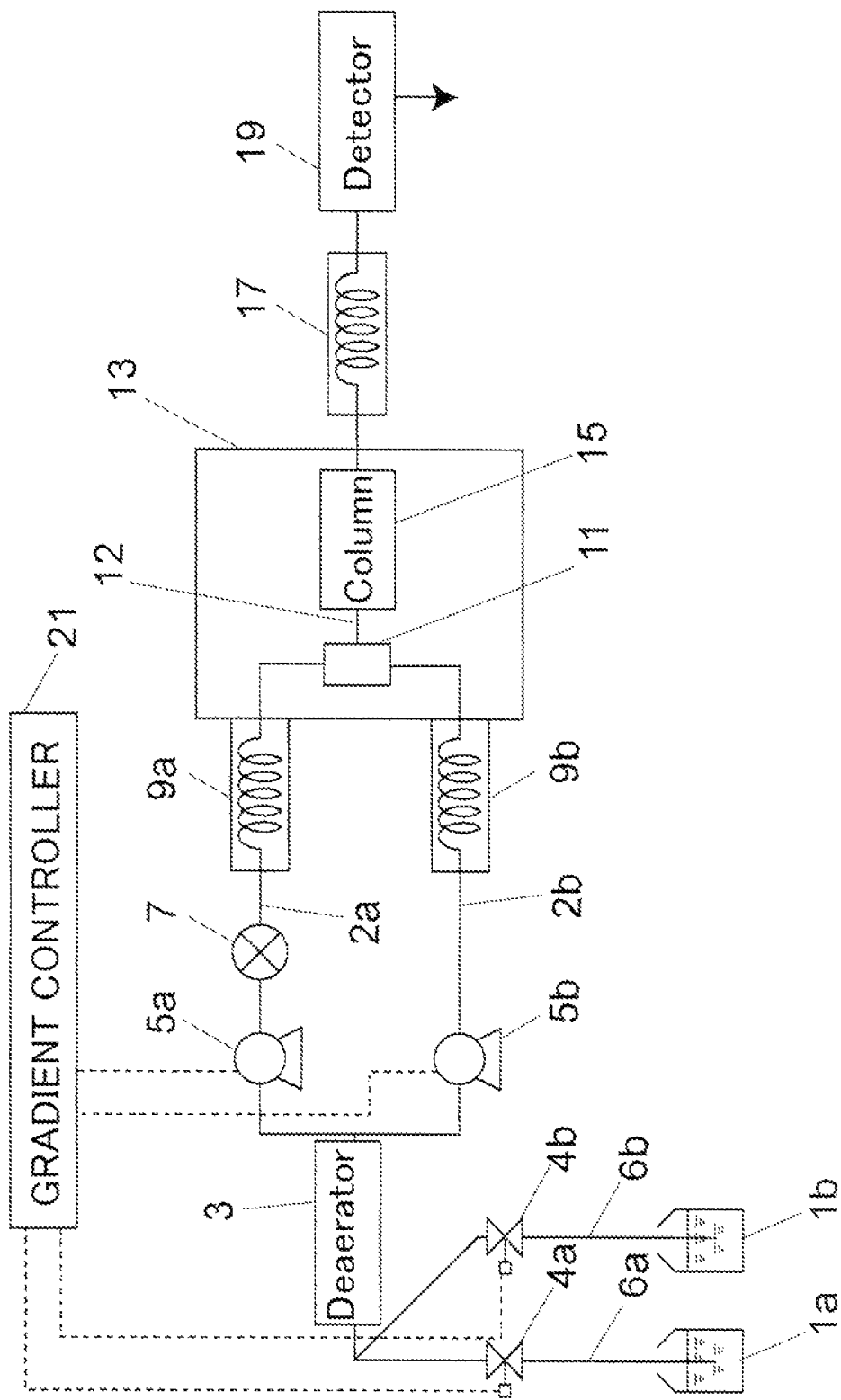
FIG. 3A is a diagram showing the flow channel configuration of a high-performance liquid chromatograph according to still another embodiment of the present invention.
Figure 3B:
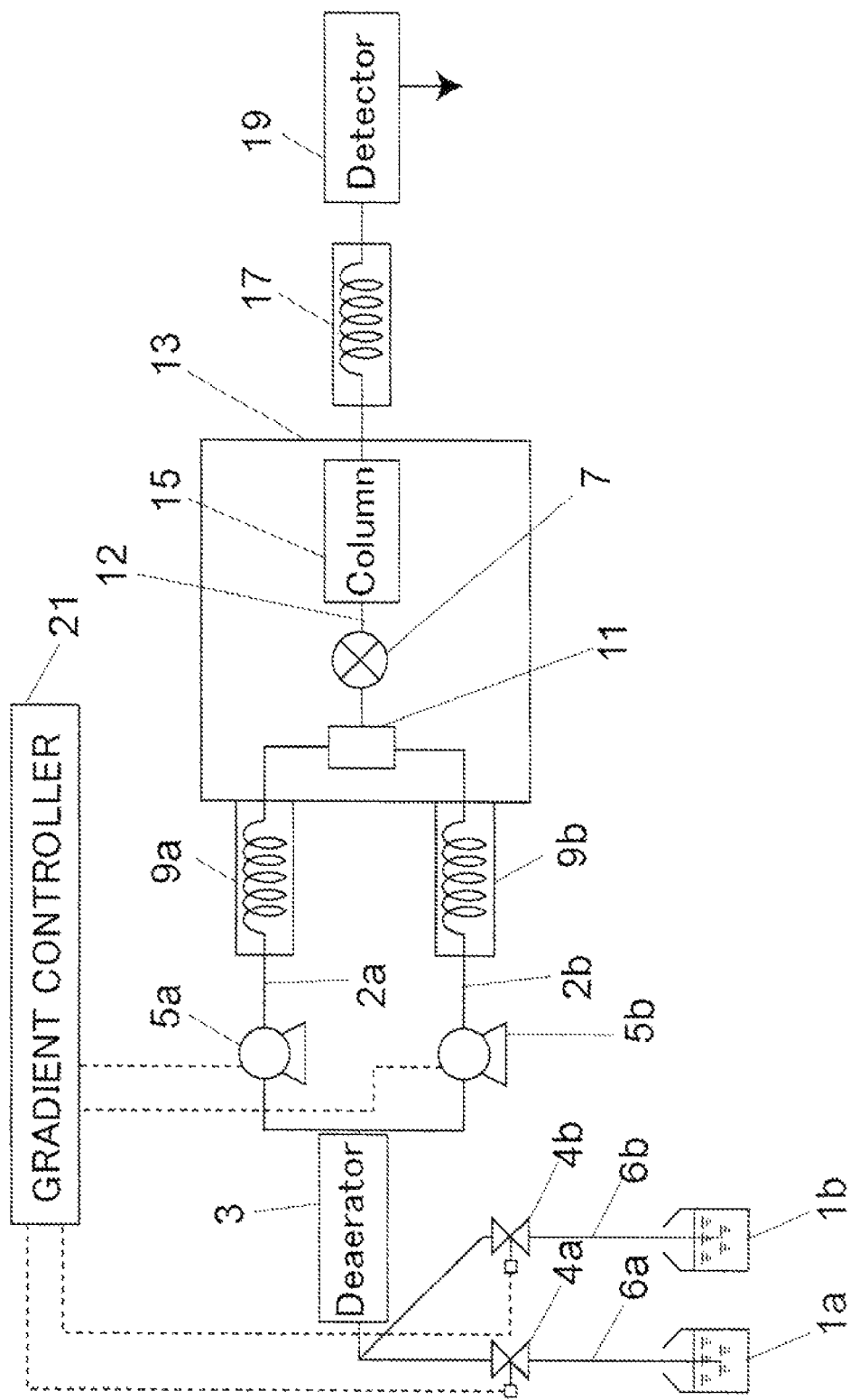
FIG. 3B is a diagram showing the flow channel configuration of a high-performance liquid chromatograph according to still another embodiment of the present invention.
Figure 4:
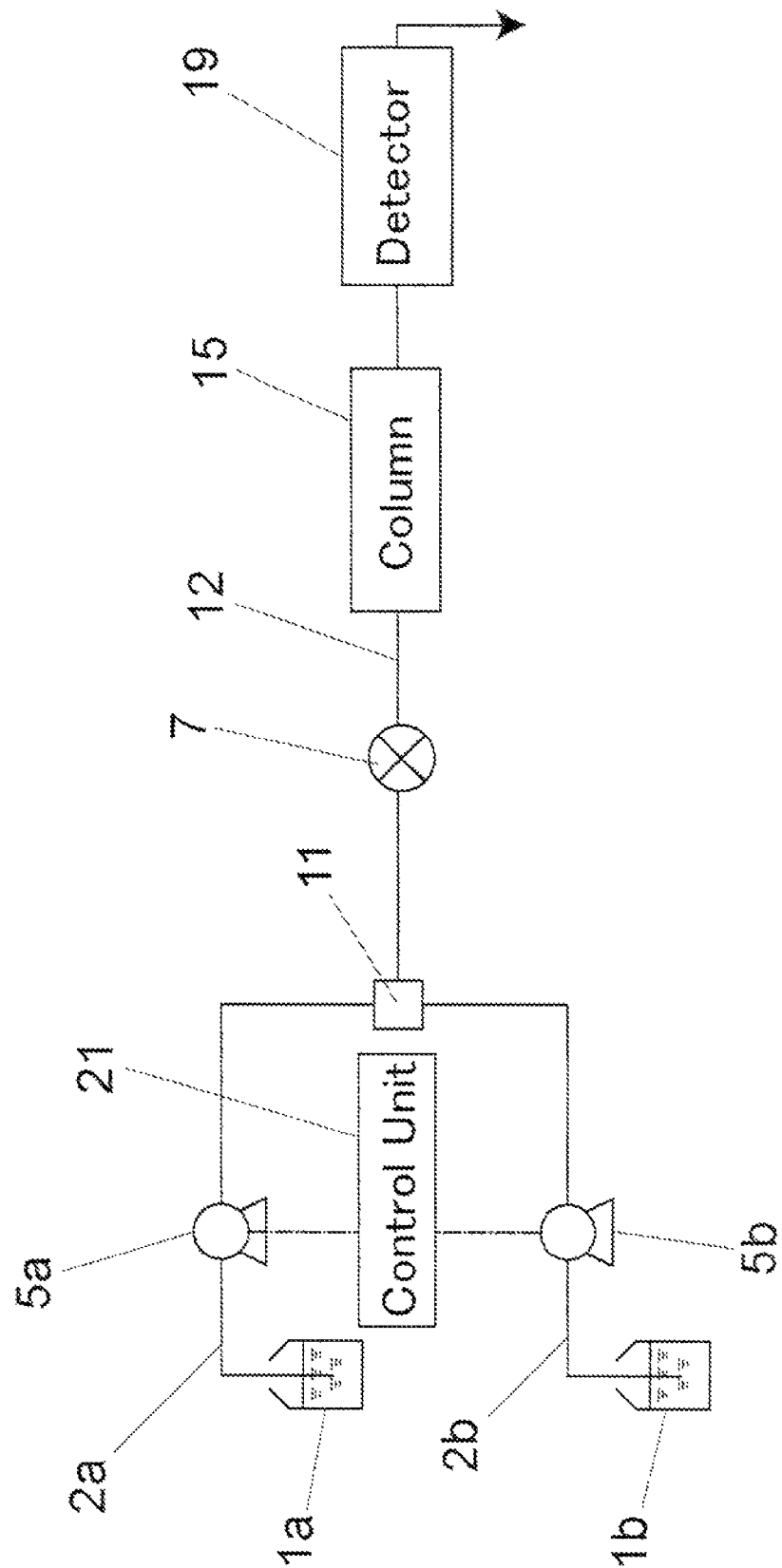
FIG. 4 is a diagram showing the flow channel configuration of a conventional high-performance liquid chromatograph having a mobile phase composition gradient system.
Figure 5:
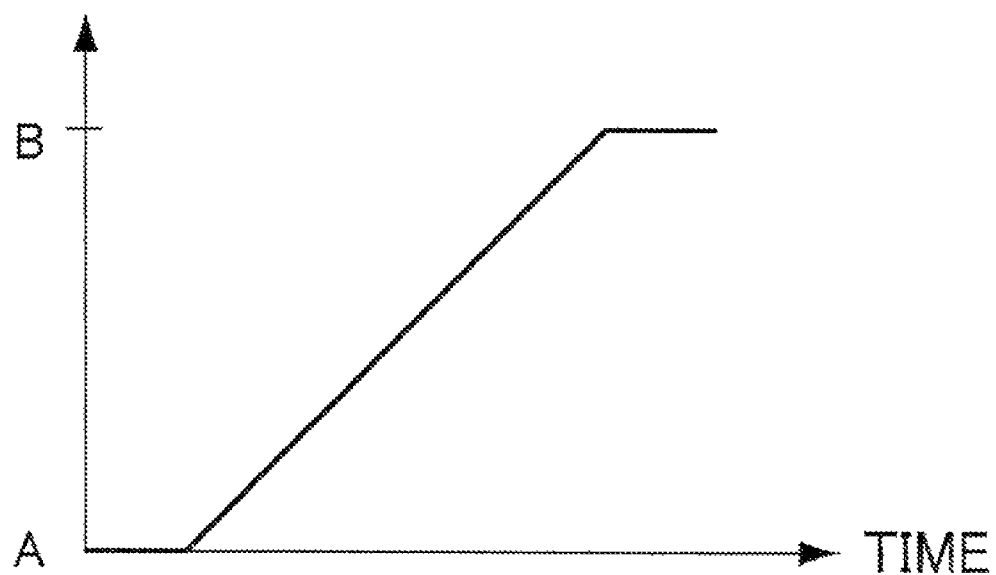
FIG. 5 is a graph showing a change in the composition of a mobile phase in mobile phase composition gradient elution.

These high-performance liquid chromatographs shown in FIGS. 3A and 3B are obtained by further connecting a mobile phase composition gradient system for changing the composition of a mobile phase with time to the high-performance liquid chromatographs for temperature gradient elution shown in FIGS. 1A and 1B, respectively.

A mobile phase 1a is connected to a flow channel 6a having a variable flow rate valve 4a, and a mobile phase 1b is connected to a flow channel 6b having a variable flow rate valve 4b. The flow channels 6a and 6b are connected to a deaerator 3, and a flow channel connected downstream of the deaerator 3 branches into two mobile phase flow channels 2a and 2b. The valves 4a and 4b are connected to a gradient controller 21 to change the proportion between the mobile phase 1a and the mobile phase 1b with time. The structures of the mobile phase flow channels 2a and 2b and other components provided downstream of the flow channels 2a and 2b are the same as those of the high-performance liquid chromatographs shown in FIGS. 1A and 1B.

As can be seen from the flow channel configurations shown in FIGS. 3A and 3B, the ratio between the flow rate of the mobile phase 1a and the flow rate of the mobile phase 1b is set to a predetermined value by changing the open area ratios of the valves 4a and 4b, and a mixture of the mobile phase 1a and the mobile phase 1b is deaerated by the deaerator 3 and then flown into the two mobile phase flow channels 2a and 2b. Thereafter, temperature gradient elution is carried out in the same manner as in the case described above with reference to FIGS. 1A and 1B.

In a case where a partition coefficient greatly varies not only with the proportion between the mobile phase 1a and the mobile phase 1b but also with temperature, by using the flow channel configuration shown in FIG. 3A or 3B, it is possible to obtain a synergistic effect between them, that is, it is possible to more greatly vary the partition coefficient. Therefore, according to the present embodiments, it is possible to provide a liquid chromatograph exhibiting a higher gradient effect.

What is claimed is:

1. A method for analysis by liquid chromatography in which a sample to be analyzed is introduced into a separation column together with a mobile phase and sample components separated by and eluted from the column are detected by a detector, the method comprising the steps of:
keeping the column adiabatic;
setting the temperature of the mobile phase supplied through one of two mobile phase flow channels to a constant temperature higher than an upper limit of a target temperature range of the mobile phase in the column and the temperature of the mobile phase supplied through the other mobile phase flow channel to a constant temperature lower than a lower limit of the target temperature range of the mobile phase in the column;
mixing two streams of the mobile phase supplied through the two mobile phase flow channels and introducing the mixed mobile phase into the column; and
changing the temperature of the mobile phase in the column over time for carrying out temperature gradient elution by changing the mixing ratio between the two streams of the mobile phase over time by regulating the flow rates of the two streams of the mobile phase flowing through the two mobile phase flow channels.

2. The method for analysis according to claim 1, wherein the mixing ratio is continuously changed over time to create a temperature gradient along the moving direction of the mobile phase in the column.

3. The method for analysis according to claim 1, wherein the temperature of an eluate from the column is adjusted to a constant temperature before the eluate is introduced into the detector.

4. The method for analysis according to claim 1, wherein the flow rates of the two streams of the mobile phase flowing through the two mobile phase flow channels are regulated so that the flow rate of the mobile phase introduced into the column becomes constant.

5. The method for analysis according to claim 1, further comprising a mobile phase composition gradient elution method in which the composition of the mobile phase supplied through the two mobile phase flow channels is changed over time.

6. A liquid chromatograph comprising:
a separation column;
a thermal insulating container for receiving the column;
a first mobile phase flow channel having a liquid sending pump and a constant-temperature unit whose temperature is set to a constant temperature higher than an upper limit of a target temperature range of a mobile phase in the column;
a second mobile phase flow channel which has a liquid sending pump different from the liquid sending pump provided in the first mobile phase flow channel and a constant-temperature unit whose temperature is set to a constant temperature lower than a lower limit of the target temperature range of the mobile phase in the column and which sends the same mobile phase as sent through the first mobile phase flow channel;
a mixer for mixing the mobile phase supplied through the first mobile phase flow channel and the second mobile phase flow channel, and sending the mixed mobile phase to the column;
a sample injector for injecting a sample to be analyzed into a flow channel for supplying the mobile phase to the column;
a detector provided downstream of the column to detect sample components separated by and eluted from the column; and
a gradient controller for regulating the flow rates of the liquid sending pumps provided in the first and second mobile phase flow channels to change the mixing ratio over time between the mobile phases in the mixer,
wherein the temperature of the mobile phase in the column is changed over time to carry out temperature gradient elution.

7. The liquid chromatograph according to claim 6, wherein the gradient controller regulates the flow rates of the liquid sending pumps provided in the first and second mobile phase flow channels in such a manner that the mixing ratio is continuously changed over time to create a temperature gradient in the column.

8. The liquid chromatograph according to claim 6, further comprising a constant-temperature unit provided between the column and the detector to adjust the temperature of an eluate from the column to a constant temperature.

9. The liquid chromatograph according to claim 6, wherein the gradient controller regulates the flow rates of the liquid sending pumps provided in the first and second mobile phase flow channels so that the flow rate of the mobile phase introduced into the column becomes constant.

10. The liquid chromatograph according to claim 6, further comprising a mobile phase composition gradient system provided in the first and second mobile phase flow channels to change the composition of the mobile phase over time.

11. The liquid chromatograph according to claim 6, wherein the sample injector is provided in the first or second mobile phase flow channel.

12. The liquid chromatograph according to claim 6, wherein the sample injector is provided in a flow channel provided between the mixer and the column.

* * * * *